Feb. 16, 1960 E. S. BOERNER Plant Pat. 1,910
ROSE PLANT
Filed June 8, 1959
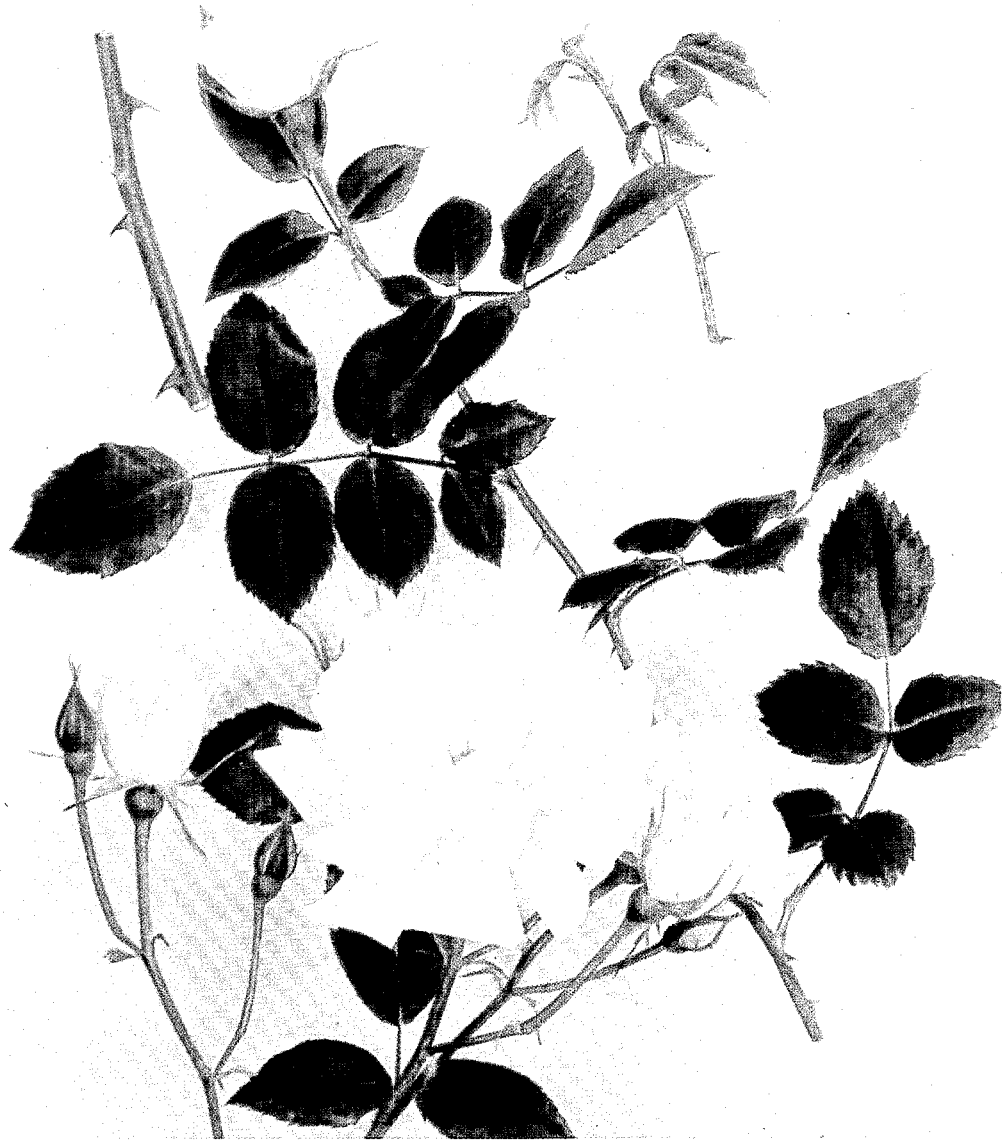
Inventor.
E. S. Boerner
By: Robb & Robb
Attorneys.

United States Patent Office

Plant Pat. 1,910
Patented Feb. 16, 1960

1,910

ROSE PLANT

Eugene S. Boerner, Newark, N.Y., assignor to Jackson & Perkins Company, Newark, N.Y., a corporation of New York Application June 8, 1959, Serial No. 818,989

1 Claim. (Cl. 47—61)

The present invention relates to a new and distinct variety of rose plant of the large-flowered polyantha class, which was originated by me by crossing the variety "Glacier" (Plant Patent No. 1,025) with the variety "Garnette" (unpatented).

The primary objective of this breeding was to produce an improved white floribunda rose having stiffer flower petals and longer lasting characteristics. This objective was fully achieved, along with other desirable improvements, by crossing the white floribunda variety "Glacier," with the variety "Garnette," which is noted for its stiff petals and long-lasting qualities. The result attained the following unique combination of characteristics which are outstanding in the new variety and which distinguish it from its parents, as well as from all other varieties of which I am aware:

(1) A habit of bearing flowers in large clusters, with the individual flowers ranging in size between those of the parents;

(2) Stiff flower petals;

(3) A pure white flower color; and (4) A long lasting quality of the flowers, both when cut and when left on the bush, with consequent exceptional decorative value, as attributed to the long lastingness of the flowers.

A sexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Glacier."
*Pollen parent.*—"Garnette."

Classification:
*Botanic.*—Large-flowered polyantha.
*Commercial.*—Floribunda.

*Flower*

(Observations made from specimens grown in a greenhouse at Newark, New York, in the early afternnon during the early part of January.)

Blooming habit: Recurrent—continuous.

Bud:
*Size.*—Medium.
*Form.*—Ovoid; is not affected by wet or hot weather.
*Color.*—When sepals first divide—Light Dull Green-Yellow, Plate 17. When petals begin to unfurl—Ivory Yellow, Plate 30, very lightly overcast with Hermosa Pink, Plate 1. When halfblown: inside of petals—Marguerite Yellow, Plate 30, with edge of petals lightly overcast with Hermosa, Pink, Plate 1; reverse of petals—White, Plate. 53.
*Sepals.*—Branched; curl back when petals begin to unfurl. Color: inside—Absinthe Green, Plate 31; outside—Deep Dull Yellow-Green, Plate 32.
*Calyx.*—Color—Deep Dull Yellow-Green, Plate 32. Shape—pear. Size—small. Aspect—smooth. Odor when rubbed—none.
*Peduncle.* — Length — medium. Aspect — smooth. Strength—bending; slender. Color—Parrot Green, Plate 6.
*Opening.*—Opens up well; is not affected by adverse weather conditions.

Bloom:
*Size.*—Medium. Average size when fully expanded—3¼ inches.
*Borne.*—Several together, and in irregular and large clusters.
*Stems.*—Medium length; normal strength.
*Form (when first open).*—Cupped. Permanence—retains its form to the end.
*Petalage.*—Double (full but open center). Number of petals under normal conditions—from 30 to 35.
*Color.*—Center of flower—Marguerite Yellow, Plate 30, with edge of petals faintly overcast with Hermosa Pink, Plate 1. Outer petals—White, Plate 53. Base of petals (aiglet)—Primrose Yellow, Plate 30. Inside of petals—White, Plate 53, with outer edge of petals faintly overcast with Hermosa Pink, Plate 1. Reverse of petals—White, Plate 53. General tonality from a distance—White, Plate 53.
*Discoloration.*—General tonality at end of first day—White, Plate 53, with outer edge of petals faintly overcast with Hermosa Pink, Plate 1. Second day—White, Plate 53. Third day—White, Plate 53.

Petals:
*Texture.*—Leathery; stiff; is not affected by wet or hot weather.
*Appearance.*—Inside—satiny. Outside—shiny.
*Form.*—Oval; slightly notched.
*Arrangement.* — Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On the plant—very long. As cut flower—very long.

*Genital organs*

Stamens, anthers: Small; many; regularly arranged around styles. Color—Amber Yellow, Plate 16.
Stamens, filaments (threads): Medium length. Color—Citron Yellow, Plate 16.
Pollen: Color—Massicot Yellow, Plate 16.
Styles: Bunched; uneven length; medium length; thin.
Stigmas: Color—Colonial Buff, Plate 30.
Ovaries: All enclosed in calyx.
Hips: None.
Seeds: None.

*Plant*

Form: Bush.
Growth: Vigorous; upright.
Foliage: Compound of 5 to 7 leaflets.
*Size.*—Medium.
*Quantity.*—Normal.

*Color.*—New foliage: upper side—Lettuce Green, Plate 5; under side—Oil Green, Plate 5, lightly overcast with Mineral Red, Plate 27. Old foliage: upper side—Forest Green, Plate 17; under side—Light Elm Green, Plate 17.

*Shape.*—Oval pointed.

*Texture.*—Upper side—glossy. Under side—smooth.

*Ribs and veins.*—Ordinary.

*Edge.*—Serrated (saw-toothed).

*Serration.*—Single; small.

*Leaf stem.*—Color—Brick Red, Plate 13. Under side—prickly.

*Stipules.*—Medium length; bearded.

Wood:

*New wood.*—Color:—Biscay Green, Plate 17. Bark—smooth.

*Old wood.*—Color—Elm Green, Plate 17. Bark—smooth.

Thorns:

*Thorns.*—Quantity: on main stalks from base—ordinary; on laterals from stalk—ordinary.

Form—flat base; medium length; hooked downward. Color (when young)—Old Rose, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by the unique combination of a habit of bearing flowers in large clusters, with the individual flowers ranging in size between those of "Glacier" (Plant Patent No. 1,025) and "Garnette" (unpatented), superior stiffness of the flower petals, pure White color of the flowers, and long-lasting qualities of the flowers, both when cut and when on the bush, with attendant exceptional decorative value of the flowers.

No references cited.